United States Patent [19]

Ohzeki et al.

[11] 4,239,803

[45] Dec. 16, 1980

[54] ETHYLENE POLYMER COMPOSITION

[75] Inventors: Toshio Ohzeki, Urawa; Mitsuo Akutsu, Tokyo; Yutaka Nakahara, Iwatsuki; Tohru Haruna, Okegawa; Motonobu Minagawa, Koshigawa; Masahiro Nonoyama, Shiraoka, all of Japan

[73] Assignee: Argus Chemical Corporation, Brooklyn, N.Y.

[21] Appl. No.: 806,511

[22] Filed: Jun. 14, 1977

[30] Foreign Application Priority Data

Jun. 17, 1976 [JP] Japan .................. 51-71427

[51] Int. Cl.³ .......................................... C07C 153/09
[52] U.S. Cl. ........................ 428/379; 174/110 PM; 260/45.85 H; 260/45.85 T; 260/45.85 S; 252/402; 252/406; 560/138; 560/140; 560/141; 560/145; 560/86
[58] Field of Search ............... 560/138, 140, 141, 86, 560/145; 260/45.85 S, 45.85 H, 45.85 T; 174/110 PM, 110 SR; 428/379; 252/402, 406

[56] References Cited

U.S. PATENT DOCUMENTS

| 2,397,960 | 4/1946 | Gribbins et al. | 260/45.85 |
| 3,459,704 | 8/1969 | Peterson et al. | 260/45.85 |
| 3,629,194 | 12/1971 | Onishi | 260/45.85 |
| 3,637,809 | 1/1972 | Kleiner | 260/45.85 |
| 3,758,549 | 9/1973 | Dexter et al. | 560/2 |
| 3,763,095 | 10/1973 | Di Battista | 260/45.85 |
| 3,773,812 | 11/1973 | Schutze et al. | 560/140 |
| 3,857,876 | 12/1974 | Jones et al. | 560/145 |
| 4,020,042 | 4/1977 | Cottman | 260/45.85 |
| 4,125,515 | 11/1978 | Kuczkowski | 560/145 |

FOREIGN PATENT DOCUMENTS 48-101435 12/1973 Japan .

Primary Examiner—Jane S. Myers
Attorney, Agent, or Firm—Otto S. Kauder

[57] ABSTRACT

A composition for enhancing and maintaining mechanical properties such as tensile strength of an ethylene polymer on heating at elevated temperature comprises (A) an initiator of cross-linking having a half-life measured at 110° C. of 0.1 to 50 hours and (B) an alkylthioalkylenecarboxylic acid ester of a polycarbocyclic polyhydric phenol.

18 Claims, No Drawings

ETHYLENE POLYMER COMPOSITION

BACKGROUND OF THE INVENTION

This invention relates to ethylene polymer compositions having enhanced mechanical properties such as tensile strength and able to maintain these enhanced properties when exposed to high temperatures. Such ethylene polymer compositions are particularly useful as insulation for conductors of electricity.

The outstanding mechanical and electrical properties of ethylene polymers are well known. Ethylene polymers are excellent insulators. They are tough and pliable, and remain so over a wide range of temperatures that encompass both cold and warm conditions found in actual use. They resist attack by water, acids, bases, oils and greases, as well as microorganisms.

The tendency to degrade under thermal-oxidation conditions that ethylene polymers have in common with most organic materials can be controlled by the use in ethylene polymers of stabilizing additives, sometimes termed antioxidants, in modest amounts. The pioneer disclosures of antioxidants for ethylene polymers include the disclosures of phenolic compounds by W. Happoldt in U.S. Pat. No. 2,448,799 of Sept. 7, 1948; thiodipropionate esters by M. Gribbins in U.S. Pat. No. 2,519,755 of Aug. 22, 1950; organic phosphites by A. Hecker in U.S. Pat. No. 2,860,115 of Nov. 11, 1958; organotin mercaptides by W. Leistner in U.S. Pat. No. 3,015,644 of Jan. 2, 1962; and combinations of sulfur compounds such as thioethers and disulfides with carbon black and/or high molecular weight phenolic compounds by W. Hawkins in U.S. Pat. No. 2,889,306 of June 2, 1959. Instead of itemizing the many subsequent disclosures of stabilizing additives for ethylene polymers whose number is staggeringly large, reference is made to the review by L. Nass in "Encyclopedia of Polymer Science and Technology" (N. Bikales, executive editor; J. Wiley-Interscience Publishers, New York), Volume 12 (1970), pages 728 to 737. Nass lists chemicals used on a commercial scale and classifies these and others by the chemical way in which they are believed to function. Nass writes:

"At the moment, there are five methods which have been employed, usually in combination with each other, to inhibit degradation of these polymers (i.e. polyolefin resins).

(1) The use of so-called "primary antioxidants," usually hindered phenols or alkylarylamines, which function mainly by trapping free radicals or by functioning as labile hydrogen donors, and thus interrupting the propagation reactions.

(2) The use of so-called "secondary antioxidants," which consist of organosulfur compounds for the most part, eg, sulfides or thioethers, disulfides, mercaptans, sulfoxylates. These act as peroxide decomposers, combining with hydroperoxides to render them inactive.

(3) The inclusion of inhibitors of color formation, such as tertiary phosphites or phosphonates. These are believed to react preferentially with the oxidized residue of the "primary" antioxidant, thus discharging the color of the typical quinoid bodies. They may also function as peroxide decomposers.

(4) The use of chelating agents or "deactivators" to trap and inactivate trace metal cations since the presence of metallic impurities is considered objectionable. Heavy-metal cations are believed to function as initiators or catalysts for the homolytic cleavage of peroxides into propagating radicals.

(5) The use of ultraviolet-radiation absorbers or other radiation screens or filters to suppress the formation of photoinitiated free radicals."

As already stated, the properties of ethylene polymers are excellent for practical service conditions. The thermoplastic nature of ethylene polymers, however, represents a deficiency in properties with respect to electrical insulation in certain emergency situations. A conductor overheated as a result of an overload or short circuit can reach temperatures of 160° C. and higher at which insulation consisting of ethylene polymer plastic can melt and flow away from the conductor, leaving areas of bare metal which can cause severe electrical fires and other serious damage. To overcome this problem, ethylene polymers have been subjected to treatments that result in cross-linking the polymer and thereby increase the tensile strength of the polymer both at ambient temperatures and especially at elevated temperatures. The first cross-linking treatments were done by exposure to high energy ionizing radiations as discovered by A. Charlesby (Proceedings of the Royal Society, London, 1952, Vol. 215A, Pages 187-214).

Later, the simpler method of cross-linking initiated by the thermal decomposition of added chemical initiators such as organic peroxides and azo compounds was introduced. The improvement in high temperature mechanical properties obtainable by cross-linking an ethylene polymer was demonstrated by S. Bonotto (Journal of Applied Polymer Science, 1965, Vol. 9, Page 3822) as shown:

TABLE I

| | | Crosslinked, Unfilled Polyethylene | | | | | | | | |
|---|---|---|---|---|---|---|---|---|---|---|
| | Melt $PE^E$ longation, % | Ultimate tensile strength psi | | (23° C.), | | Secant modulus, content, | | Yield strength mole/cm$^3$ | Gel | Cross-linking density factor c, |
| Polymer | index | 23° C. | 160° C. | 23° C. | 160° C. | 23° C. | 160° C. | psi | % | $\times 10^{-3a}$ |
| Low-density $PE^b$ | 2 | 1,800 | Flows | 600 | Flows | 20,000 | Flows | 1,200 | — | — |
| Crosslinked low-density $PE^b$ (3% peroxide$^c$) | 0 | 2,280 | 66 | 500 | 100 | 11,000 | 166 | d | 88.3 | 0.16 |
| Crosslinked low-density $Pe^b$ (4.5% peroxide$^c$) | 0 | 2,360 | 118 | 490 | 100 | 10,400 | 237 | d | 88.3 | 0.23 |
| Crosslinked low-density | | | | | | | | | | |

TABLE I-continued

Crosslinked, Unfilled Polyethylene

| Polymer | Melt PE$^E$-longation, % index | Ultimate tensile strength psi 23° C. | 160° C. | (23° C.), 23° C. | 160° C. | Secant modulus, content, 23° C. | 160° C. | Yield strength mole/cm.$^3$ psi | Gel % | Cross-linking density factor c, × 10$^{-3a}$ |
|---|---|---|---|---|---|---|---|---|---|---|
| PE$^b$ (3% peroxide,$^c$ 10% triallyl cyanurate) | 0 | 2,350 | 66 | 193 | 15 | 11,350 | 445 | d | 93.0 | 0.43 |
| High-density PE$^e$ | 5 | 3,000 | Flows | 270 | Flows | 150,000 | Flows | 4,600 | — | — |
| Crosslinked high-density PE$^e$ (3% peroxide$^c$) | 0 | 2,300 | 245 | 265 | 80 | 55,000 | 474 | 2,400 | 98.0 | 0.45 |
| Vulcanized rubber$^f$ | 0 | 2,200 | 170 | 350 | 40 | 705 | 600 | d | 87.7 | 0.57 |

$^a$See Experimental Section.
$^b$DYNH, density 0.919.
$^c$Dimethyl peroxide: cured at 160° C., 15 min.
$^d$No true yield point.
$^e$DMD-7000, density 0.96.
$^f$SBR formulation: SBR rubber (100), HAF black (50), sulfur (1.33), Altax (1.0) cumate (0.16).

Similarly Bonotto has shown that cross-linking by the action of 1.5% 2-phenyl-2-propyl peroxide (dicumyl peroxide) at 160° C. increases the 23° C. tensile strength of ethylene-ethyl acrylate copolymer from 1910 psi (130 kg per square cm) to 2980 psi (230 kg per square cm) for the crosslinked polymer. More significantly the crosslinked polymer retains 50 psi (3.4 kg per square cm) tensile strength at 160° C. while the unmodified polymer flows at 160° C.

Disclosures of various initiators and methods for the cross-linking of ethylene polymers with the help of chemical additives include the use of peroxides decomposing above the melting point of the polymer, by H. Haeberli in Swiss Pat. No. 475,083 of Aug. 29, 1969; acetylenic bis-peroxycarbonic acid diesters, for example 2,5-dimethyl-2,5-bis(ethoxycarbonylperoxy)-3-hexyne, by O. Mageli in U.S. Pat. No. 3,297,738 of Jan. 10, 1967; acetylenic bis-dialkyl peroxides, such as 2,5-bis(t-butyl-peroxy)-2,5-dimethyl-3-hexyne, by H. Blanchard in U.S. Pat. No. 3,334,080 of Aug. 1, 1967; the same hexyne as well as the saturated analog 2,5-bis(t-butylperoxy)-2,5-dimethylhexane by M. Narkis in Journal of Applied Polymer Science 1969, Vol. 13, Pages 713–720, and the latter two as well as bis(1,3-di-t-butylperoxyisopropyl)benzene by Dr. Braun in Chemical Abstracts 1971, Vol. 74, 64508 g.

Unfortunately, the improvement in mechanical properties of ethylene polymers achieved through cross-linking has much increased the difficulty of safeguarding the properties of the polymer once its fabrication and shaping into end products such as electrical insulation is completed, in order to prevent premature deterioration of the product. Use of stabilizing additives and antioxidants as practiced with ethylene polymers that are not subjected to cross-linking is ineffective or inapplicable in the case of the cross-linked polymers. As summarized by Nass, stabilizers are effective because they decompose peroxides that form as a result of antioxidation or because they interrupt the propagation of chain reactions involving free radicals. This means that the customary stabilizers can and do destroy peroxides used as initiators of cross-linking and are themselves destroyed as well. Thus the search for a stabilizing additive that can be compounded with an ethylene polymer that is cross-linked chemically and protect the properties thereof is a problem entirely different from that of stabilizing thermoplastic ethylene polymers. For example, D. Simunkova et al (Chemical Abstracts 1970, vol. 73, No. 88573c) reported on the dicumyl peroxide initiated cross-linking of polyethylene in the presence of the antioxidants 2,2'-methylene bis(4-methyl-6-t-butylphenol), dilauryl thiodipropionate, zinc mercaptobenzimidazole, and phenylbeta-napthylamine. The authors observed that interaction of antioxidants with free radicals lowered both the efficiency of cross-linking and the oxidation stability of the polymer.

A. Bluestein, et al (Chemical Abstracts, 1968, Vol. 68, No. 30555f) reported on the effectiveness of polymerized trimethyldihydroquinoline as a high temperature antioxidant for cross-linked polyethylene. The authors note that many different forms of the antioxidant are available and results obtained vary depending on which form is used.

R. Catte in German Offenlegungschrift No. 2,062,603 of June 24, 1971 (see Chemical Abstracts 1971, vol. 75, No. 110816b) disclosed a synergistic antioxidant combination of a phenol for example 2,6-di-t-butyl-4-methyl-phenol, with a 1,2-dihydroquinoline and an organic zinc salt, for example zinc mercaptobenzothiazole, zinc dimethyl-dithiocarbamate, and zinc mercaptobenzimidazole.

General Electric Co. in British Pat. No. 871,284 of June 28, 1961 disclosed a curable polyethylene containing dicumylperoxide and 1,2-dihydro-2,2,4-trimethyl-quinoline as antioxidant.

M. Watanabe et al in Japan Publication No. 10516/64 of June 13, 1964 disclosed cross-linking polyethylene composition with an organic peroxide as cross-linking agent, an antioxidant and 4,4'-thio-bis(6-t-butyl-m-cresol) as radical acceptor.

K. Tezika et al in Japan Publication No. 18461/74 of May 10, 1974 disclosed cross-linking polyethylene composition by incorporating 4,4'-thiobis(6-t-butyl-3-methyl phenol), sulfur and di(ortho-benzamide phenyl) disulfide into polyethylene containing an organic peroxide.

A. DiBattista in U.S. Pat. No. 3,763,095 of Oct. 2, 1973 disclosed stabilized cross-linking polyethylene with a bisphenol sulfide having the formula (1):

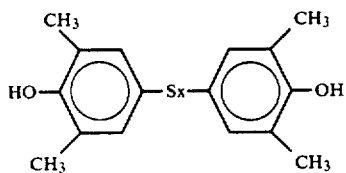

(I)

In addition to the large number of thiodipropionate esters disclosed as ethylene polymer stabilizers since the pioneer disclosure of M. Gribbins, a variety of esters containing the thioalkylenecarboxylic acid ester structure have been disclosed. Among these, H. Braus in U.S. Pat. Nos. 3,504,012 of Mar. 31 and 3,538,047 of Nov. 3, 1970 disclosed 2-hydroxyethyl 3,5-di-t-butyl-4-hydroxybenzylthiopropionate. H. Eggensperger in U.S. Pat. No. 3,832,838 of Aug. 27, 1974 disclosed hydroxydialkylbenzylthioalkanecarboxylic acid ester having the formulae:

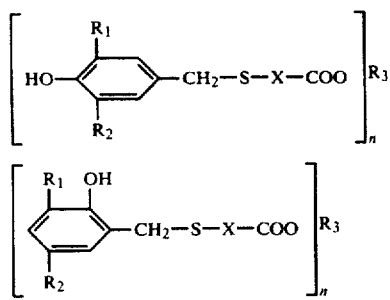

(Ia)

(Ib)

wherein
n is an integer from 1 to 4,
$R_1$ and $R_2$ are the same or different linear or branched alkyl groups having preferably 1 to 6 C atoms,
$R_3$ is a linear, branched or cyclic alkyl sulfur oxygen interrupted alkyl, phenyl, benzyl or phenyl having alkyls of 1 to 9 carbons (if n=1) or an alkylene group (if n=2), alktriyl (if n=3) and alktetrayl (if n=4), containing 1–20 C atoms, whereby said groups may be substituted for n=1, —$C_2H_4$— for n=2,

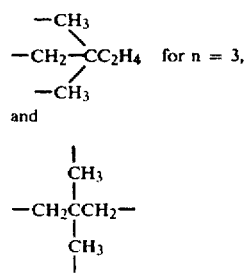

for n=4 and X is a linear or branched lower alkylene group.

M. Minagawa in Japan Kokai 101435/73 of Dec. 20, 1973 disclosed polymer stabilizers having the formula R—O—A—O—R, in which there can be one or more —A— group and A can be a residue of a dicarboxylic acid, a polyhydric phenol or a polyhydric alcohol; R and R', can be alkyl or R'CO where R'CO is a residue of a monocarboxylic acid. The only monocarboxylic acids shown are stearic acid, salicylic acid, and 3(3,5-di-t-butyl-4-hydroxyphenyl)propionic acid.

H. Schutze in U.S. Pat. No. 3,630,991 of Dec. 28, 1971 disclosed non-exuding and non-volatile sulfur containing esters of cyclic terpene alcohols for the stabilization of 2 to 8 carbon alpha-olefin polymers together with hindered phenols. Schutze's esters may be represented by the structural formulae ROOC $CH_2(CH)_n SR_a$ ROOC $CH_2(CH_2)_n SS (CH_2)_n CH_2 COOR'$ $$ROOCCH_2(CH_2)_n \overset{O}{\overset{\|}{S}}(CH_2)_n CH_2 COOR'$$

ROOC $CH_2(CH_2)_n S(CH_2)_n S(CH_2)_n CH_2 COOR'$

ROOC $CH_2(CH_2)_n S(CH_2)_n S(CH_2)_m CH_3$ where
$R_a$ is —$CH_2(CH_2)_n COOR'$ or alkyl
n=1 to 5
m=1 to 16
R is a radical selected from the group consisting of abietyl, hydroabietyl, tetrahydroabietyl, dihydroabietyl, dihydroabietyl, dihydropimaryl, tetrahydropimaryl, borneyl, alpha-terpineyl, B-terpineyl, V-terpineyl, methyl, and dihydroterpineyl, and
R' is a radical selected from the group consisting of abietyl, hydroabietyl, tetrahydroabietyl, dihydroabietyl, dehydroabietyl, dihydropimaryl, tetrahydropimaryl, borneyl, alpha-terpineyl, B-terpineyl, methyl, and dihydroterpineyl.

A. Onishi, in U.S. Pat. No. 3,629,194 of Dec. 21, 1971 disclosed a polyolefin resin stabilized against thermal aging with esters of alkyl thiopropionic or alkyl thiobutyric acid with a polyol having up to five hydroxyl groups, in combination (optionally) with a phenolic antioxidant. The alkyl thiopropionic or alkyl thiobutyric acid esters are defined as having one of the formulae:

| | |
|---|---|
| R—$SC_n H_{2n} COOR'OOCC_n H_{2n} SR$ | (1) |
| $RSC_n H_{2n} COOC_m H_{2m} SC_m H_{2m} OOCC_n H_{2n} SR$ | (2) |
| R"C—$(CH_2 OX)_3$ | (3) |
| $CH_2 OX$ | (4) |
| $\|$ | |
| HC—OX | |
| $\|$ | |
| $CH_2 OX$ | |
| and | |
| C—$(CH_2 OX)_4$ | (5) | wherein
R is an alkyl of 8 to 30 carbon atoms,
m and n are each integers of 2 or 3,
R' is an alkylene containing 2 to 12 carbon atoms,
R" is an alkyl containing 1 to 20 carbon atoms,
X is hydrogen or —OC—$C_n H_{2n} SR$, at least one of which is —OCC$_n$H$_2$ $_n$SR,
the $R_1$, R' and R" moieties in one compound being the same or different.

The phenolic antioxidants are defined by Onishi as mono- or polyhydric phenolic compounds in which at least one of the ortho positions to a hydroxyl group is substituted by an alkyl, aralkyl, or cycloalkyl group.

The substituents preferably contain carbon atoms of a number of the order of 3 to 10, and the alkyl group, atoms inclusive of that in an aralkyl and cycloalkyl groups can be unsaturated. The phenolic compounds may be further substituted, and the phenolic compounds may be polyphenolic compounds such as bisphenolic, trisphenolic, or tetrakisphenolic compounds in which phenolic nuclei are connected by a connecting group such as an alkylene, a thioether, or a triazinoxyl group.

M. Dexter in U.S. Pat. No. 3,758,549 of Sept. 11, 1973 disclosed alkyl esters derived from alkyl thioalkanoic acids and alkane polyols, such as pentaerythritol tetrakis, 3-n-dodecylthiopropionate, and ethylene-bis-3-n-dodecylthiopropionate. These are used in combination with phenolic antioxidants to effectively stabilize polyolefins from the deleterious effects of heat and oxygen. The alkyl esters are defined by the formula:

$$\left( R-S-CH_2CH_2\overset{O}{\overset{\|}{C}}O \right)_n Z$$

wherein

R is an alkyl group of from one to eighteen carbon atoms, n has a value of from 2 to 4; and Z is an aliphatic hydrocarbon of the formula:

$$C_yH_{2y+2-n}$$

in which y has a value of from 2 to 18 when n is 2 and a value of from 3 to 6 when n is greater than 2, the value of y in all cases being equal to or greater than that of n.

M. Minagawa in Japanese Kokai No. 75/106881 of Aug. 27, 1975 disclosed stabilized resin compositions containing 3-alkylthiopropionate esters of alcohols containing a nitrogen-heterocyclic ring, for example tris(2-hydroxyethyl isocyanurate) and optionally a phenolic antioxidant.

SUMMARY OF THE INVENTION

In accordance with this invention, ethylene polymers having mechanical properties such as tensile strength at elevated temperatures enhanced over that of modified ethylene polymers and maintained at a high level over long periods of aging at an elevated temperature are obtained by compounding an ethylene polymer with a composition comprising (A) at least one initiator of cross-linking having a half life measured at 110° C. in the range from 0.1 to 50 hours and (B) at least one ester of an alkylthioalkylenecarboxylic acid with a polycarbocyclic polyhydric phenol having the formula:

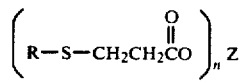

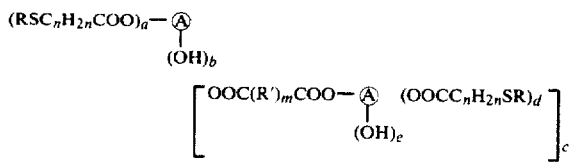

in which R is an alkyl group having from 1 to 32 carbon atoms, 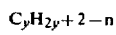 is a polycarbocyclic phenol group, R' is an alkylene, phenylene, alkenylene, alkenylenethioalkene, alkylenedithioalkylene, or alkylenethioalkylenethioalkylene group having 1 to 12 carbon atoms, m is 0 or 1, n is an integer from 1 to 5, a is an integer from 1 to 4, and b, c, d, and e are independently assigned integers from 0 to 3, provided that the sum of a, b, and c is an integer from 2 to 4 and, when c is not zero, the sum of d and e is an integer from 1 to 3. The compounding operation is performed at a temperature at which the initiator of cross-linking is stable or decomposed to a small extent only, suitably 100°–125° C. After compounding, the ethylene polymer is subjected to higher temperatures, suitably 140°–200° C., at which the initiator decomposes and cross-linking takes place. A shaping operation can intervene between compounding and cross-linking; for example, the compounded ethylene polymer can be extruded over a conductor of electricity to form a sheath that is subsequently cross-linked to provide a high temperature resistant insulated conductor.

The concentration of initiator used is in the range from about 0.2 to about 5% by weight of the ethylene polymer, and the concentration of the alkylthioalkylenecarboxylic acid ester of polycarbocyclic polyhydric phenol is in the range from about 0.005 to about 5% by weight of the ethylene polymer. Accordingly, the relative weight proportions of the initiator to the ester range from about 1000 to 1 to 1 to 5.

DESCRIPTION OF THE PREFERRED EMBODIMENTS

Ethylene polymers whose mechanical properties are enhanced according to this invention include low density polyethylene (a homopolymer of ethylene), high density polyethylene (also a homopolymer of ethylene), and copolymers of ethylene as the major monomer representing about 75% or more of the polymer with at least one minor monomer representing no more than about 25% of the polymer. Suitable minor monomers include propylene, 1-butene, 1-hexene, vinyl acetate, and ethyl acrylate. Blends of the ethylene homopolymers and copolymers here recited can be used.

The initiator of cross-linking having a half-life measured at 110° C. in the range from 0.1 to 50 hours can be organic peroxide and an organic azo compound. The half life is defined as the time period required at a specified temperature to diminish the initial concentration to one half the initial value; the half life is usually measured in an organic solvent solution having a concentration approximating the intended use concentration in the polymer of interest, for example 5% by weight in toluene.

Initiators of cross-linking that can be used include benzoyl peroxide, t-butylperoxy-2-ethylhexanoate, t-butylperoxy-2-methylpentanoate, p-chlorobenzoyl peroxide, t-butyl peroxyisobutyrate, t-octyl peroxy o-chlorobenzoate, t-butyl peroxy-4-t-butylcyclohexyl carbonate, 1,1-bis(t-butyl peroxy)cyclohexane, 2,2-bis(4,4-di-t-butylperoxycyclohexyl)propane, 2,5-dimethyl-2,5-di(n-octanoylperoxy)hexane, 1,1-bis(t-butylperoxy)3,5,5-trimethylcyclohexane, t-butylperoxy-3,5,5-trimethylhexanoate, t-butylperoxy isopropyl carbonate, t-butylperoxycrotonate, 2,5-dimethyl 2,5-dibenzoylperoxy)hexane, 2,5-dimethyl-2,5-di(benzoylperoxy)hexyne-3,2,2-bis(t-butylperoxy)butane, t-butylperoxybenzoate, di-t-butylperoxyphthalate, t-butylperoxy-p-chlorobenzoate, n-butyl 4,4-bis(butylperoxypentanoate), ethyl 3,3-bis(t-butylperoxybutanoate), di(2-phenyl-2-propyl)peroxide, 2,5-dimethyl-2,5-di(t-butylperoxy)hexane, t-butyl 2-phenylpropyl peroxide, 2,5-dimethyl-2,5-di(t-butylperoxy)hexyne-3, di(2-t-butylperoxypropyl)benzene, t-butyl hydroperoxide, di-isopropylbenzene dihydroperoxide, di-t-butyl peroxide, p-menthane hydroperoxide, t-octyl hydroperoxide, cumene hydroperoxide, benzenesulfonazide, azobis(isobutyronitrile), azobis(1-cyanocyclohexane), azodicarboxylic acid diethyl ester, and azodicarbonamide. Combinations of two or more initiators can be used, for example t-butylhydroperoxide with di-t-butylperoxide.

The ester component (B) of the composition of this invention is a new ester of an alkylthioalkylenecarboxylic acid with a polycarbocyclic polyhydric phenol. The ester is derived from an alkylthioalkylenecarboxylic acid having the formula $RSC_nH_{2n}CO_2H$, in which R is an alkyl group having from 1 to 32 carbon atoms and n is an integer from 1 to 5, and a polycarbocyclic polyhydric phenol having the formula $(A)(OH)_{a+b+c}$ in which (A) is a two-, three-, or four-functional phenolic nucleus having 2 to 4 benzenoid rings connected by direct linkages or through oxygen, sulfur, or aliphatic hydrocarbon, cycloaliphatic hydrocarbon, or hydroxyaryl-substituted aliphatic hydrocarbon groups; a is an integer from 1 to 4, and b and c are integers from 0 to 3, provided that the sum of a+b+c is an integer from 2 to 4. The benzenoid rings of the polycarbocyclic polyhydric phenol can be substituted by alkyl or cycloalkyl groups having from 1 to about 10 carbon atoms. The ester can also contain dicarboxylic acid ester groups derived from one or more dicarboxylic acids having the formula $HOOC(R')_mCOOH$ in which R' is an alkylene, phenylene, alkenylene, alkylenethioalkylene, alkylenedithioalkylene, or alkylenethioalkylenethioalkylene group having 1 to 12 carbon atoms, and m is 0 or 1. Dicarboxylic acids that can be used include oxalic acid, malonic acid, succinic acid, maleic acid, glutaric acid, adipic acid, decane dicarboxylic acid, 1,12-dodecane dicarboxylic acid, thiodiglycolic acid, thiodipropionic acid, dithiodipropionic acid, phthalic acid, terephthalic acid, and methylene bis (thioglycolic acid). The R alkyl groups can be straight or branched chain and include methyl, ethyl, isopropyl, n-butyl, isobutyl, t-butyl, hexyl, 2-ethylhexyl, n-octyl, decyl, n-dodecyl, t-dodecyl, tridecyl, n-hexadecyl, n-octadecyl, eicosyl, docosyl, octacosyl, and triacontanyl. Alkylthioalkylenecarboxylic acids that can be used in the form of their polycarboxylic polyhydric phenol esters include S-2-methylthioacetic acid, 2-ethylthioacetic acid, 2-ethylthiopropionic acid, 3-n-butylthiopropionic acid, 4-(2-ethylhexylthio)butanoic acid, 3-n-octylthio-2-methylpropionic acid, 2-n-dodecylthiopropionic acid, 2-n-tetradecylthioacetic acid, 5-n-hexadecylthiopentanoic acid, and 4-docosylthio-4-methylbutanoic acid.

Useful alkylthioalkylenecarboxylic acid esters of polycarbocyclic polyhydric phenols according to this invention include esters of bisphenols having two phenolic nuclei linked directly or through a two valent hydrocarbon group such as 2,2'-methylene bis(p-cresol), 2,2'-methylene bis(4-methyl-6-t-butyl-phenol), 2,2'-methylene bis(4-ethyl-6-t-butylphenol), 2,2'-methylene bis(4-methyl-6-(1-methylcyclohexyl)phenol), 2,2'-n-butylidene bis(4,6-dimethylphenol), bis-1,1-(2'-hydroxy-3'5'-dimethylphenyl)-3,5,5-trimethylhexane, 2,2'-cyclohexylidene bis(4-ethyl-6-t-butylphenol), 2,2'-isopropylbenzylidene bis(4-ethyl-6-t-butylphenol), 4,4'-bis(2,6-di-t-butylphenol), 4,4'-dihydroxy-biphenyl, 3,4-di(4-hydroxyphenyl)hexane, 4,4'-methylene-bisphenol, 2,2'-n-octylidene bis(4-methylphenol), 2,2'-bis(4'-hydroxyphenyl)heptane, 4,4'-methylenebis(2-methyl-6-t-butylphenol), 4,4'-methylene bis(2,6-di-t-butylphenol), 4,4'-n-butylidene bis(3-methyl-6-t-butylphenol), 4,4'-cyclohexylidene bis(2-t-butylphenol), 4,4'-cyclohexylidene bis(2-cyclohexylphenol), 4,4'-benzylidene bis(2-t-butyl-5-methylphenol), 4,4'-isopropylidenediphenol, 4,4'-cyclohexylidene-bisphenol and 4,4'-cyclohexylidene bis(2,3,6-trimethylphenol).

Another preferred class of alkylthioalkylenecarboxylic acid esters that can be used according to this invention is the class of esters of preferably ortho-substituted bisphenols having two phenolic nuclei linked through oxygen or sulfur, such as 4,4'-oxobisphenol, 4,4'-oxobis(3-methyl-6-isopropylphenol), 2,2'-oxobis(4-dodecylphenol), 4,4'-thiobis(2-methyl-6-t-butylphenol), 4,4'-thiobis(3-methyl-6-t-butylphenol), 4,4'-thiobisphenol, 4,4'-sulfobis(3-methyl-6-t-butylphenol), bis(2-methyl-4-hydroxy-5-t-butylbenzyl)sulfide, bis(3,5-di-t-butyl-4-hydroxy benzyl) sulfide, 2,2'-thiobisphenol, 2,2'-thiobis(4-t-butyl-6-methylphenol), 2,2'-thiobis(4-methyl-6-t-butyl-phenol), and 2,2'-thiobis(4,6-di-t-butyl-phenol).

A particularly preferred class of alkylthioalkylenecarboxylic acid esters according to this invention is the class of esters of preferably ortho-substituted phenols having three or four phenolic nuclei, such as 1,1,3-tris(2'methyl-4'-hydroxy-5'-t-butylphenyl)butane, 1,3,5-tris(3',5'-di-t-butyl-4'-hydroxybenzyl)-2,4,6-trimethylbenzene, 2,2-bis(3'-t-butyl-4'-hydroxyphenyl)-4-(3'',5''-di-t-butyl-4''-hydroxyphenyl)butane, and 2,2-bis(2'methyl-5'-t-butyl-4'-hydroxyphenyl)-4-(3'',5''-di-t-butyl-4''-hydroxyphenyl) butane, 2,6-bis(2'-hydroxy-3'-t-butyl-5'-methylbenzyl)-4-methylphenol, and 2,2-bis(4,4,4',4'-tetrakis-p-hydroxyphenyl)cyclohexyl) propane.

A number of esters of alkylthioalkylenecarboxylic acids with polycarboxylic polyhydric phenol according to this invention are shown below in Table 1. In the formulas, the symbol X indicates a t-butyl group.

TABLE 1

No. 1: 4,4'-Butylidenebis(2-t-butyl-5-methylphenyl 3-dodecanethiopropionate) a=2, b=c=d=e=0

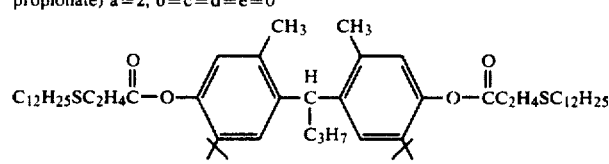

No. 2: 2,2'-Methylenebis(4-methyl-6-t-butylphenol)mono-3-dodecanethiopropionate a=1, b=1, c=d=e=0

TABLE 1-continued

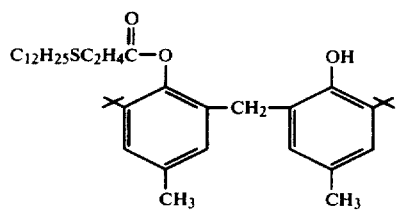

No. 3: 4,4'-Methylenebis(2-t-butyl-6-methylphenyl-3-dodecanethiopropionate) a=2, b=c=d=e=0

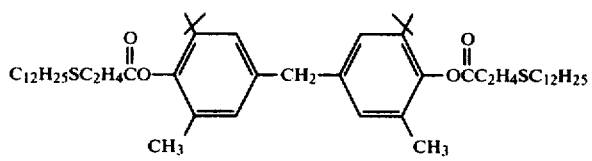

No. 4: 4,4'-Methylenebis(phenyl 3-dodecanethiopropionate) a=2, b=c=d=e=0

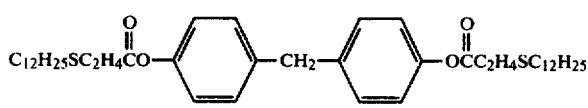

No. 5: 4,4'-Thiobis(2,6-dimethylphenyl 3-butanethiopropionate) a=2, b=c=d=e=0

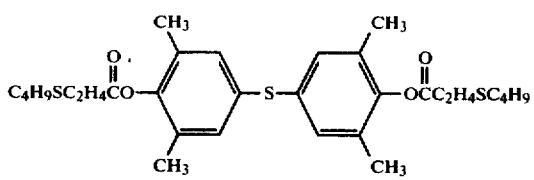

No. 6: 4,4'-Thiobis(2-t-butyl-5-methylphenyl 3-dodecanethiopropionate) a=2, b=c=d=e=0

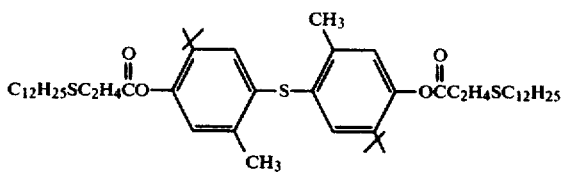

No. 7: Bis(2-methyl-5-t-butyl-4(4-dodecanethiobutanoyloxy)benzyl) sulfide a=2, b=c=d=e=0

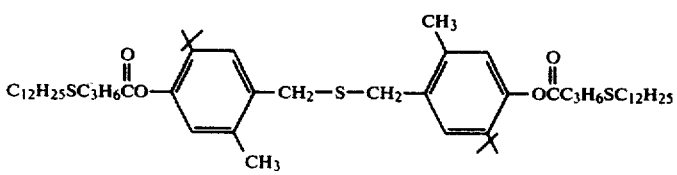

No. 8: 2,2'-Thiobis(4-methyl-6-t-butylphenol)mono-3-octadecanethiopropionate a=1, b=1, c=d=e=0

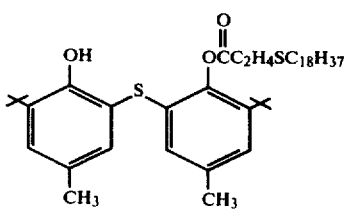

No. 9: 1,1,3-Tris(2-methyl-5-t-butyl-4(3-dodecanethiopropionyloxyphenyl)butane a=3, b=c=d=e=0

TABLE 1-continued

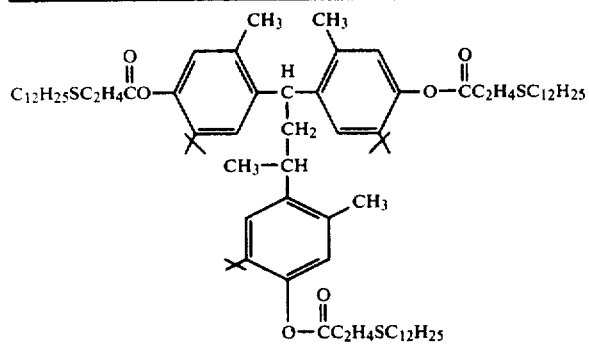

No. 10: 1(3,5-Di-t-butyl-4-hydroxyphenyl)-3,3-bis(3-dodecanethiopropionyl-oxyphenyl)butane a=2, b=1, c=d=e=0

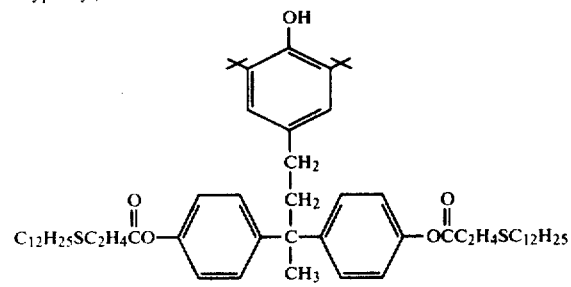

No. 11: 1-(3,5-Di-t-butyl-4-hydroxyphenyl)-3,3-bis(2-methyl-5-t-butyl-4(3-dodecanethiopropionyloxy)phenyl)butane a=2, b=1, c=d=e=0

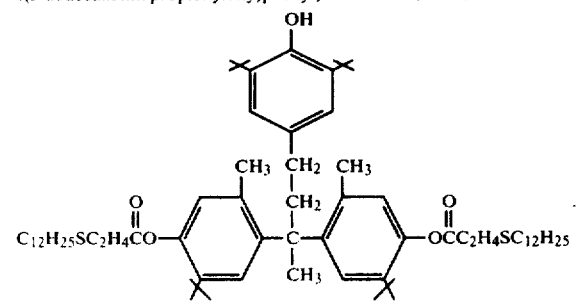

No. 12: Bis(3-octadecanethiopropionyloxyphenylthio)phenyl adipate
a=1, b=0, c=1, d=1, e=0

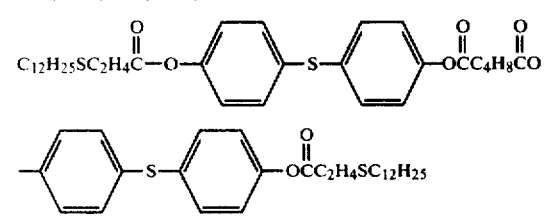

No. 13: Bis(4,4'-butylidenebis(2-t-butyl-5-methylphenol)thiodipropionate mono-3-dodecanethiopropionate a=1, b=0, c=1, d=0, e=1

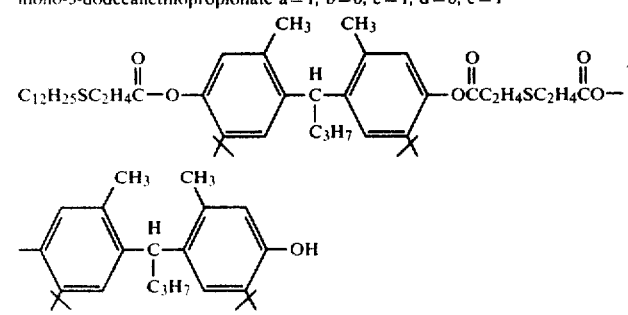

No. 14: Bis(3-dodecanethiopropionyloxy-2-t-butyl-5-methylphenylthio-2-t-butyl-5-methylphenyl)thiodipropionate a=1, b=0, c=1, d=1, e=0

TABLE 1-continued

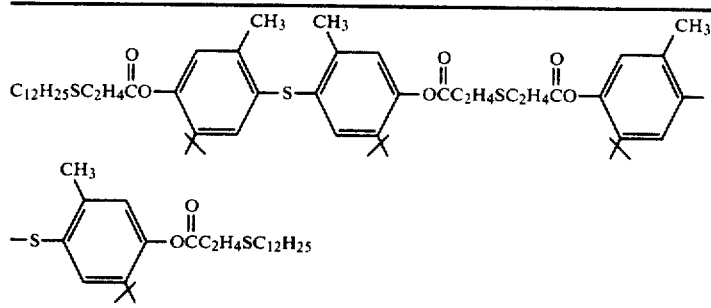

No. 15: Thiodipropionate diester of 1(3,5-di-t-butyl-4-hydroxyphenyl)-
3,3-bis(3-t-butyl-4-hydroxyphenyl)butane mono-3-dodecanethio-
propionate a=1, b=1, c=1, d=1, e=1

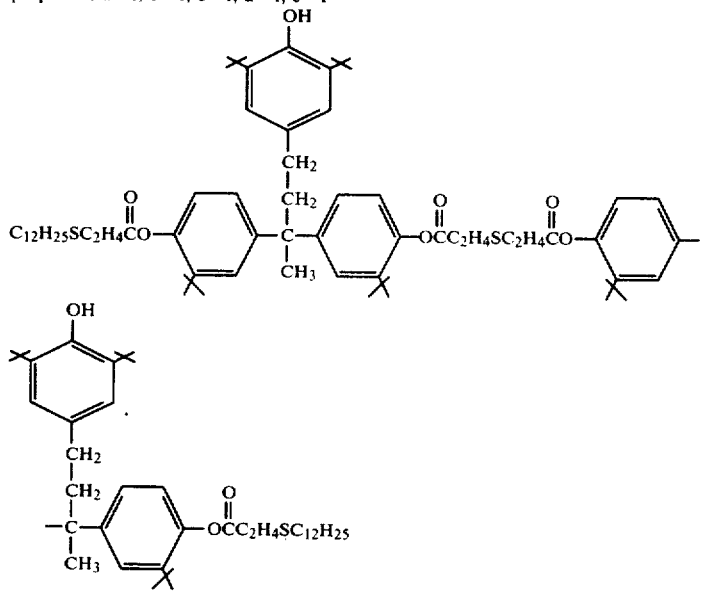

No. 16: Thiodipropionate diester of 4,4,4',4'-tetrakis(3-t-butyl-4-
hydroxyphenyl) dicyclohexylpropanetris(3-dodecanethiopropionate)
a=3, b=0, c=1, d=3, e=0

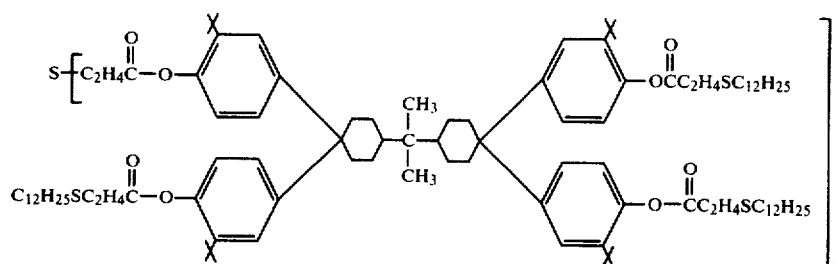

No. 17: 4,4'-Thiobis(2-t-butyl-5-methylphenol)mono-3-dodecanethiopropionate
a=1, b=1, c=d=e=0

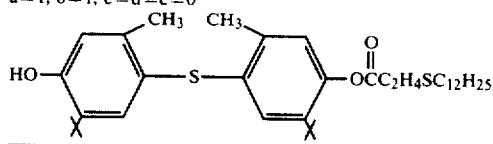

Several convenient techniques are available for preparing the new esters of alkylthioalkylenecarboxylic acids with polycarbocyclic polyhydric phenols. The alkylthioalkylenecarboxylic acid and polycarbocyclic polyhydric phenol starting materials are known compounds or are readily prepared by known methods. Direct esterification of an alkylthioalkylenecarboxylic acid with a polycarbocyclic polyhydric phenol can be carried out at temperatures in the 150°–210° C. range in the presence of moderately strong acidic catalysts such as phosphoric acid, phosphorous acid, diphenyl phosphite, triphenyl phosphite, sulfamic acid, and toluenesulfonic acid; use concentrations of these acidic catalysts can range from 0.1 to about 2% by weight of the reactants. Water produced as the side product of the esterification can be removed with an azeotroping solvent or by vacuum distillation. The crude ester can be refined by washing with water and aqueous alkali metal bicarbonate solution to remove acid catalyst and small amounts of unreacted alkylthioalkylenecarboxylic acid. Aqueous-alcoholic alkali can be used to separate polycarbocyclic polyhydric phenols fully esterified with alkylthioalkylenecarboxylic acid from partly esterified phenols having one or more free phenolic hydroxyl groups, but this separation is not always necessary since both types of esters are effective according to this invention and can be utilized in admixture with one another.

Alkylthioalkylenecarboxylic acid esters of polycarbocyclic polyhydric phenols of this invention can also be prepared by transesterification of an alkylthioalkylenecarboxylic acid with an ester of a polycarbocyclic polyhydric phenol under conditions where equilibrium is established and then displaced in the desired direction by removal of by-product. Suitably, a lower aliphatic carboxylate ester such as a formate or acetate of the polycarbocyclic polyhydric phenol is used. The transesterification reaction can be carried out in the 100°–200° C. range and the by-product lower aliphatic carboxylic acid removed by distillation at atmospheric or subatmospheric pressure. Suitable catalysts for this transesterification include the moderately strong acids already recited; alkaline reacting materials such as sodium carbonate, potassium acetate, barium hydroxide, and the alkali and alkaline earth metal salts of the alkylthioalkylenecarboxylic acids and polycarbocyclic polyhydric phenol being reacted; heavy metal and metal organic compounds such as stannous oxalate, stannous oleate, zinc acetate, manganese acetylacetonate, tetrabutyl titanate, and di-n-octyltin oxide.

Another suitable method for preparing alkylthioalkylenecarboxylic acid esters of polycarbocyclic polyhydric phenols utilizes an acid chloride of an alkylthioalkylenecarboxylic acid. The acid can be converted to the acid chloride by the action of a chlorinating agent such as thionyl chloride, phosphorus trichloride, oxalyl chloride, or benzotrichloride. Frequently the acid chloride need not be isolated from the reaction of the acid with the chlorinating agent and can be used directly.

The reaction of an alkylthioalkylenecarboxylic acid chloride with a polycarbocyclic polyhydric phenol can be carried out without auxiliary chemicals at temperatures ranging from 45° to 180° C. Vacuum, an inert gas sparge, or the action of a boiling inert solvent such as heptane or toluene can be used to assist the evolution and removal of the by-product hydrogen chloride.

Alternatively, the reaction of an alkylthioalkylenecarboxylic acid chloride with a polycarbocyclic polyhydric phenol can be carried out in the presence of an acid acceptor under relatively mild conditions, typically at temperatures from −10° to 120° C. Acid acceptors can be aliphatic and aromatic tertiary amines, for example trimethylamine, triethylamine, and diethylaniline; heterocyclic nitrogen bases such as pyridine, N-methylpiperidine and N-ethylmorpholine; aqueous alkaline solutions of sodium or potassium hydroxide; suspensions of sodium, potassium, and calcium carbonates and bicarbonates in inert solvents, and others. The following preparations of alkylthioalkylenecarboxylic acid esters of polycarbocyclic polyhydric phenols according to this invention are illustrative.

EXAMPLE A: Preparation of 1,1,3-tris(2-methyl-4(S-dodecylthiopropionyloxy)-5-t-butylphenyl)butane (Table 1, Compound No. 9)

54.4 g of 1,1,3-tris(2-methyl-4-hydroxy-5-t-butylphenyl) butane and 33.3 g of triethylamine were dissolved in 300 ml of benzene, and 96.5 g of 3-n-dodecylthiopropionic acid chloride was added dropwise to the solution at room temperature. After the addition, the reaction was continued for more 2 hours.

The reaction mixture was filtered and then washed with water to remove triethylamine hydrochloride, dried, and the solvent removed. A pale yellow liquid compound was obtained, having refractive index (RI) 1.5170 at 25° C.

Nuclear magnetic resonance and infra-red spectra were consistent with the assigned structure.

Similarly prepared compounds and their properties are shown in Table 2.

TABLE 2

| EX. | COMPOUND NO. Table 1 | PHYSICAL PROPERTIES |
|---|---|---|
| B | 6 | Pale Yellow Liquid, RI (25° C.) 1.5219 |
| C | 17 | Pale Yellow Liquid, RI (25° C.) 1.5342 |

In compounding ethylene polymer compositions according to this invention, suitable precautions are applied to avoid prematurely exposing the initiator of cross-linking to excessive temperatures at which immediate decomposition of a large fraction of the initiator might occur. At the compounding temperatures of ethylene polymers according to this invention (typically 100°–125° C.), the initiator is substantially unaffected in the required relatively brief process time. The heat transfer surfaces of process equipment, however, are usually at a considerably higher temperature, and it is therefore important to avoid contact of heated equipment with an initiator in concentrated form. Suitably, therefore the initiator of cross-linking is pre-mixed or master-batched with at least a small quantity of the ethylene polymer in a powdered form, typically between 2 and 10% of the whole charge and if desired the alkylthioalkylenecarboxylic acid ester of polycarbocyclic polyhydric phenol and other additives such as pigments, fillers, and stabilizers, can be included in the same pre-mix or masterbatch. The pre-mix containing the initiator can then be compounded with the remaining portions of the ethylene polymer and alkylthioalkylenecarboxylic acid ester and other desired additives (if not already incorporated) in any desired manner on conventional equipment such as heated mixing rolls, single screw and multi-screw extruders, Banbury mixers, and calenders. Compounded ethylene polymer containing an initiator of cross-linking and alkylthioalkylenecarboxylic acid ester of polycarbocyclic polyhydric phenol according to this invention can be granulated, ground, or extruded and pelletized for storage or transportation if desired before being further processed at a higher temperature at which cross-linking takes place and the enhanced mechanical properties are obtained according to this invention. A particularly useful manner of processing ethylene polymers according to this invention is the preparation of insulated electrical conductors by extruding the ethylene polymer composition in the form of a cover for the conductor at temperatures not higher than about 125° C., and subsequently subjecting the insulated conductor to heat treatment at 140° to 200° C. until cross-linking has occurred.

Ethylene polymers comprising an initiator of cross-linking and an alkylthioalkylenecarboxylic acid ester of a polycarbocyclic polyhydric phenol according to this invention can contain in addition conventional compounding ingredients as desired, including pigments such as titanium dioxide, carbon black, iron oxides, molybdate orange, and blue and green phthalocyanines; fillers such as talc, mica, clays, and precipitated chalk; stabilizers including phenolic antioxidants, thiodipropionate esters, and copper deactivators. Stabilizers when used in conjunction with the composition of this invention are used in quantities small enough not to interfere with the action of the initiator of cross-linking, typically less than 2% by weight of the ethylene polymer. Phenolic antioxidants that can be used include 2,6-di-t-butyl-4-methylphenol, tetrakis 3-(4'-hydroxy-3',5'-di-t-butylphenyl) propionyloxymethyl)methane, and 1,3,5-tris(3,5-di-t-butyl-4-hydroxybenzyl)isocyanurate. A comprehensive disclosure of phenolic antioxidants that can be used provided by M. Minagawa at column 19 line 27 to column 25 line 68 of U.S. Pat. No. 3,997,551 is here incorporated by reference. Thiodipropionate diesters that can be used include dimethyl thiodipropionate, di-isodecyl thiodipropionate, and distearyl thiodipropionate. A comprehensive disclosure of thiodipropionates that can be used by M. Minagawa at column 26 line 1 to column 28 line 37 of U.S. Pat. No. 3,997,551 is here incorporated by reference.

Copper deactivators that can be included in the ethylene polymers of this invention counteract the prodegradant effect of traces of copper compounds. Useful copper deactivators include oxalic acid dianilide, oxalic acid bis (benzylidene hydrazide) and 3-salicyloylamino-1,2,4-triazole. A comprehensive disclosure of copper deactivators by M. Minagawa column 2 line 8 to column 15 line 43 of U.S. Pat. No. 3,997,551 is here incorporated by reference.

The groups of Examples that follow illustrate, without limiting the scope thereof, the incorporation according to this invention in ethylene polymers of an initiator of cross-linking and an alkylthioalkylenecarboxylic acid ester of a polycarbocyclic polyhydric phenol, the advantageous mechanical properties obtained and their maintenance upon heating at elevated temperatures for long periods.

EXAMPLE 1-1 to 1-12

Powdered unstabilized polyethylene (crosslinking grade low-density polyethylene of melt flow index 2.0) 100 parts by weight and sample compounds (Table 2) 0.4 parts by weight were blended by mixing and machine grinding for 10 minutes at ambient temperature. The compositions were then kneaded on a two roll mill at 110° C. for 10 minutes; dicumylperoxide (Percumyl D, made by Nippon Oil Fats Co., Ltd.) 2.0 parts by weight was added and kneaded at the same temperature for 2 minutes more. The milled sheet was compression molded for 5 minutes at 110° C. and 100 kg/cm², heated rapidly to 180° C. and sheets of 1 mm in thickness prepared by maintaining the pressure of 100 kg/cm², for 15 minutes. One such sheet was cut to the size of 40 × 150mm, hung in the Geer air circulating oven and heat-aged in an air atmosphere at 160° C. The deterioration time was defined as the time until more than 50% of the pieces from a particular sample were discolored or distorted. The results are shown in Table 3. Another such sheet of each composition was tested for tensile strength and elongation to determine the adequacy of crosslinking.

Esters according to this invention used in these Examples are referred to by their reference number in Table 1.

TABLE 3

| | SAMPLE COMPOUND (loadings by weight) | DETERIORATION TIME (Hours at 160° C.) |
|---|---|---|
| No. Control | | |
| 1-1 | 2,6-di-t-butyl-4-methylphenol (0.4) | 12 |
| 1-2 | 4,4'-thiobis(3-methyl-6-t-butylphenol) (0.4) | 56 |
| 1-3 | Tetrakis 3-(4'-hydroxy-3',5'-di-t-butylphenyl) propionyloxymethyl methane (0.4) | 18 |
| 1-4 | Dilaurylthiodipropionate (0.4) | 10 |
| 1-5 | 2,6-di-t-butyl-4-methylphenol (0.2) dilaurylthiodipropionate (0.2) | 32 |
| 1-6 | 4,4'-thiobis(3-methyl-6-t-butylphenol) (0.2) dilaurylthiodipropionate (0.2) | 64 |
| Example | | |
| 1-1 | No. 1 (Table-1) (0.4) | 158 |
| 1-2 | No. 6 (Table-1) (0.4) | 192 |
| 1-3 | No. 12 (Table-1) (0.4) | 164 |
| 1-4 | No. 14 (Table-1) (0.4) | 188 |
| 1-5 | No. 6 (Table-1) (0.3) 2,6-di-t-butyl-4-methylphenol (0.1) | 214 |
| 1-6 | No. 8 (Table-1) (0.3) 4,4'-thiobis(3-methyl-6-t-butylphenol) (0.1) | 205 |
| 1-7 | No. 14 (Table-1) (0.3) dilaurylthiodipropionate (0.1) | 210 |
| 1-8 | No. 5 (Table-1) (0.3) distearylthiodipropionate (0.1) | 204 |
| 1-9 | No. 3 (Table-1) (0.2) dilaurylthiodipropionate (0.1) 2,6-di-t-butyl-4-methylphenol (0.1) | 193 |
| 1-10 | No. 7 (Table-1) (0.2) distearylthiodipropionate (0.1) Tetrakis 3-(4'-hydroxy-3',5'-di-t-butylphenyl-propionyl methane (0.1) | 210 |
| 1-11 | No. 15 (Table-1) (0.2) Tetrakis(laurylthiopropionyloxymethyl) | |

TABLE 3-continued

| SAMPLE COMPOUND (loadings by weight) | | DETERIORATION TIME (Hours at 160° C.) |
|---|---|---|
| | methane (0.1) | 198 |
| | 2,6-di-t-butyl-4-methylphenol (0.1) | |
| 1-12 | No. 6 (Table-1) (0.15) | |
| | dilaurylthiodipropionate (0.1) | 204 |
| | 2,6-di-t-butyl-4-methylphenol (0.05) | |
| | 3-salicyloylamino-1,2,4-triazole (0.1) | |

As shown by tensile strength measurements, all samples of Examples 1—1 to 1-12 according to the invention and Controls were adequately crosslinked.

The results of the heat aging test show that each of the samples containing an ester according to the invention are far superior in maintaining the superior physical properties generated as a result of cross-linking than any of the Control compositions.

EXAMPLES 2-1 to 2-12

Unstabilized polyethylene (melt flow index 3.7, density 0.92) 100 parts by weight, sample compounds (Table-3) 0.3 part by weight, and azodicarbonamide 15 parts by weight were blended by mixing and grinding for 10 minutes at 25°-30° C.

The composition was kneaded by a two-roll mill at 120° C. for 7 minutes and the milled sheet was compression molded at 130° C. and 100 kg/cm² for 5 minutes and thus a sheet of 1 mm thickness was prepared.

This sheet was irradiated with 5 Mrad radiation by a Cockcroft-Walton type accelerator at 40° C. This sheet was cut to the size of 100 × 250 mm, the sample pieces were hung in the Geer oven at 230° C., maintained for 7 minutes and foamed. The density of the foam obtained was about 0.06 gr/cm³. Compositions in which cross-linking was inhibited fell apart during the foaming process in the Geer oven and did not yield sample pieces. This failure to yield foamed sample pieces was judged to be bad cross-linking.

The foamed sample pieces obtained were made into No. 1 dumbbell sample pieces which were heat-aging tested for 12 days in an air-circulating oven at 150° C.

After this, the elongation after aging was measured according to the testing method of Japanese Industrial Standard K6767, and the ratio to the original elongation, i.e. retention of elongation in percent, was calculated.

The results are shown in Table- 4.

TABLE 4

| | SAMPLE COMPOUND (loadings, by weight) | Cross-Linking | ELONGATION RETENTION (%) |
|---|---|---|---|
| No. | | | |
| Control | | | |
| 2-1 | None | Good | Too small to measure |
| 2-2 | tris(3,5-di-t-butyl-4-hydroxybenzyl) isocyanurate (0.3) | Good | 8.0 |
| 2-3 | Octadecyl-3-(3,5-di-t-butyl-4-hydroxyphenyl) propionate (0.3) | Bad | — |
| 2-4 | 2,6-di-t-butyl-4-methylphenol (0.1) pentaerythritol tetrakis(lauryl mercaptopropionate) (0.2) | Good | 23.5 |
| EXAMPLE | | | |
| 2-1 | No. 2 (Table-1) (0.3) | Good | 80.7 |
| 2-2 | No. 6 (Table-1) (0.3) | Good | 89.5 |
| 2-3 | No. 8 (Table-1) (0.3) | Good | 87.0 |
| 2-4 | No. 10 (Table-1) (0.3) | Good | 82.4 |
| 2-5 | No. 12 (Table-1) (0.3) | Good | 85.9 |
| 2-6 | No. 16 (Table-1) (0.3) | Good | 83.8 |
| 2-7 | No. 2 (Table-1) (0.2) 2,6-di-t-butyl-4-methylphenol (0.1) | Good | 82.5 |
| 2-8 | No. 6 (Table-1) (0.2) Tris(3,5-di-t-butyl-4-hydroxyphenyl) isocyanurate (0.1) | Good | 91.7 |
| 2-9 | No. 4 (Table-1) (0.2) 4,4'-thiobis(3-methyl-6-t-butylphenol) (0.1) | Good | 85.4 |
| 2-10 | No. 7 (Table-1) (0.15) Dilaurylthiodipropionate (0.1) 2,6-di-t-butyl-4-methylphenol (0.05) | Good | 86.2 |
| 2-11 | No. 9 (Table-1) (0.15) Dilaurylthiodipropionate (0.1) 2,6-di-t-butyl-4-methylphenol (0.05) N-salicyloyl-N'-salicylidenehydrazine (0.1) | Good | 88.0 |
| 2-12 | No. 17 (Table-1) (0.3) | Good | 86.8 |

EXAMPLES 3-1 to 3-7

Compositions of ethylene-vinylacetate copolymer (melt flow index 2.5, vinylacetate content 10%) 100 parts by weight, sample compounds (Table-5) 0.2 parts by weight, and dicumylperoxide 2 parts by weight were kneaded at 120° C., compression molded at 180° C., and 200 kg/cm² for 15 minutes, made into a sheet of 1 mm in thickness and heat aged in a Geer oven at 150° C. for 7 days. Tensile strength before and after heat aging was measured and tensile strength retention was calculated.

The results are shown in Table 5.

All compositions had initial tensile strength above 130 kg/cm², which indicated that satisfactory cross-linking had occurred.

TABLE 5

| No. | SAMPLE COMPOUND (loadings, by weight) | TENSILE STRENGTH RETENTION (%) |
|---|---|---|
| Control | | |
| 3-1 | 4,4'-butylidene bis(3-methyl-6-t-butylphenol) (0.2) | Too little to measure |
| 3-2 | 4,4'-thiobis(3-methyl-6-t-butylphenol) (0.2) | 24 |
| EXAMPLE | | |
| 3-1 | No. 5 (Table-1) (0.2) | 68 |
| 3-2 | No. 6 (Table-1) (0.2) | 75 |
| 3-3 | No. 11 (Table-1) (0.2) | 60 |
| 3-4 | No. 13 (Table-1) (0.2) | 62 |
| 3-5 | No. 14 (Table-1) (0.2) | 71 |
| 3-6 | No. 6 (Table-1) (0.1) 4,4'-thiobis(3-methyl-6-t-butylphenol) (0.1) | 80 |
| 3-7 | No. 14 (Table-1) (0.05) 4,4'-thiobis(3-methyl-6-t-butylphenol) (0.05) dilaurylthiodipropionate (0.1) | 78 |

The results of the aging tests show that the advantageous tensile strength of ethylene-vinyl acetate copolymer compositions containing the combinations of this invention is maintained for at least 2½ times as long as with conventional combination of initiator and antioxidant.

We claim:

1. An ester of an alkylthioalkylenecarboxylic acid with a polycarbocyclic polyhydric phenol having the formula:

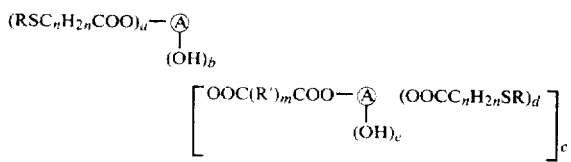

in which R is an alkyl group having from 1 to 32 carbon atoms, A is a residue of a polycarbocyclic phenol having 2 to 4 benzene rings each substituted with one phenolic hydroxyl group and connected through oxygen, sulfur, —CH₂S—CH₂—, or saturated aliphatic hydrocarbon cycloaliphatic hydrocarbon, or hydroxyaryl-substituted aliphatic hydrocarbon groups, R' is an alkylene, phenylene, alkenylene, alkylenethioalkylene, alkylenedithioalkylene, or alkylenethioalkylenethioalkylene group having up to 12 carbon atoms, m is 0 or 1, n is an integer from 1 to 5, a is an integer from 1 to 4, b, c, d, and e are integers from 0 to 3, provided that the sum of a, b, and c is an integer from 2 to 4, and when c is not zero, the sum of d and e is an integer from 1 to 3.

2. An ester according to claim 1 in which n=2.
3. An ester according to claim 1 in which a=2.
4. An ester according to claim 1 in which a=1.
5. An ester according to claim 1 in which a=3.
6. An ester according to claim 1 in which the phenol is a thiobis (alkylphenol).
7. An ester according to claim 1 in which the phenol is an alkylidenebis (alkylphenol).
8. An ester according to claim 1 in which the phenol is an alkyl-substituted trisphenol.
9. an ester according to claim 1 having the formula:

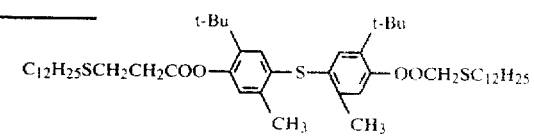

10. A composition capable of enhancing the tensile strength of an ethylene polymer upon heating at 150° C. comprising (A) at least one organic peroxide or organic azo compound initiator of cross-linking having a half-life measured at 110° C. in the range from 0.1 to 100 hours and (B) at least one ester according to claim 1, in which the portions of (A) to (B) range from 100 to 1 to 1 to 2.

11. A composition according to claim 10 in which the initiator of cross-linking is an organic peroxide.

12. A composition according to claim 11 in which the organic peroxide is bis(2-phenyl-2-propyl) peroxide.

13. A composition according to claim 10 in which the initiator of cross-linking is an organic azo compound.

14. A composition according to claim 13 in which the organic azo compound is azodicarbonamide.

15. An ethylene polymer composition having, as a result of cross-linking in the presence of at least one organic peroxide or organic azo compound initiator of cross-linking having a half-life measured at 110° C. in the range from 0.1 to 100 hours, a tensile strength of at least 130 kg/cm², comprising an ethylene polymer which is low density polyethylene, high density polyethylene, or a copolymer of at least 75% ethylene with not more than 25% of at least one co-monomer which is propylene, 1-butene, 1-hexene, vinyl acetate, or ethylene acrylate, and from 0.01 to 2% of an ester according to claim 1.

16. An ethylene polymer composition according to claim 15 in which the ethylene polymer is low density polyethylene.

17. An ethylene polymer composition according to claim 15 in which the ethylene polymer is a copolymer of ethylene and vinyl acetate.

18. An ethylene polymer composition according to claim 15 in the form of insulation on a conductor of electricity.

* * * * *